US008260582B2

(12) United States Patent
Ho et al.

(10) Patent No.: US 8,260,582 B2
(45) Date of Patent: Sep. 4, 2012

(54) METHOD FOR CHARACTERIZING LENSES

(75) Inventors: Arthur Ho, Coogee (AU); Raksha Urs, Miami, FL (US)

(73) Assignee: Vision CRC Limited, Kensington, NSW (AU)

( * ) Notice: Subject to any disclaimer, the term of this patent is extended or adjusted under 35 U.S.C. 154(b) by 558 days.

(21) Appl. No.: 12/380,213

(22) Filed: Feb. 25, 2009

(65) Prior Publication Data
US 2010/0121612 A1    May 13, 2010

Related U.S. Application Data

(60) Provisional application No. 61/199,025, filed on Nov. 12, 2008.

(51) Int. Cl.
G06F 17/50 (2006.01)
G06F 7/60 (2006.01)
G06F 17/10 (2006.01)
(52) U.S. Cl. .................................. 703/1; 703/2
(58) Field of Classification Search .............. 703/2, 1; 434/277–282
See application file for complete search history.

(56) References Cited

U.S. PATENT DOCUMENTS

| 4,356,538 | A | * | 10/1982 | Plummer ................ 362/217.02 |
| 2002/0018185 | A1 | * | 2/2002 | Kuramochi et al. ............ 353/69 |
| 2005/0068489 | A1 | | 3/2005 | Hall et al. |
| 2006/0274262 | A1 | * | 12/2006 | Andino et al. ................ 351/159 |
| 2007/0115431 | A1 | | 5/2007 | Smith, III et al. |
| 2009/0161065 | A1 | | 6/2009 | Smith, III et al. |

OTHER PUBLICATIONS

Koretz, Jane F. et al., "Analysis of Human Crystalline Lens Curvature as a Function of Accomodative State and Age", Apr. 12, 1984, Pergamon Press Ltd.*

Einighammer, Jens, "The Individual Virtual Eye", Feb. 2, 2008, pp. (xi, 26, 29, 113).*
Burd, H.J. et al., "Numerical Modeling of the Accommodating Lens", Mar. 4, 2002, Vision Research 42 (2002), Elsevier Science Ltd.*
Izatt, J.A., et al., "Micrometer-Scale Resolution Imaging of the Anterior Eye in Vivo With Optical Coherence Tomography," Archives of Ophthalmology, 1994, pp. 1584-1589, vol. 112, No. 12, XP-002557978.
Richdale, K., et al., "Lens Thickness with Age and Accommodation by Optical Coherence Tomography," Ophthalmic and Physiological Optics, pp. 441-447, Sep. 2008, vol. 28, No. 5, XP-002557979.
Wolffsohn, J. S., et al., "Anterior Opthalmic Imaging," Jul. 2006, pp. 205-214, vol. 89, No. 4, XP002557980.
Verma Y., et al., "Measurement of Gradient Refractive Index Profile of Crystalline Lens of Fisheye In Vivo Using Optical Coherence Tomography," Applied Physics B; Laser and Optics, May 25, 2007, pp. 607-610, vol. 87, No. 4.
International Search Report mailed on May 20, 2010 in PCT/US2009/035085.
Written Opinion of the International Searching Authority mailed on May 20, 2010 in PCT/US2009/035085.

(Continued)

*Primary Examiner* — Kandasamy Thangavelu
*Assistant Examiner* — Cedric D Johnson
(74) *Attorney, Agent, or Firm* — Smith Moore Leatherwood LLP

(57) ABSTRACT

Methods are disclosed for characterizing an entire lens surface including anterior and posterior 'hemispheres' as well as the equatorial region as a single continuous mathematical representation by employing a summed serial function constituting incrementally higher orders of a base function and by utilizing a sufficiently high order of base function in the summation series to obtain the desired degree of accuracy of the representation.

13 Claims, 14 Drawing Sheets
(14 of 14 Drawing Sheet(s) Filed in Color)

OTHER PUBLICATIONS

Howcroft et al., "Aspheric Curvatures for the Human Lens", Vision Res., 1977, pp. 1217-1223, vol. 17.

Koretz et al., "Analysis of Human Crystalline Lens Curvature as a Function of Accommodative State and Age", Vision Res., 1984, pp. 1141-1151, vol. 24, No. 10.

Koretz et al., "A Model for Accommodation in the Young Human Eye: The Effects of Lens Elastic Anisotropy on the Mechanism", Vision Res., 1983, pp. 1679-1686, vol. 23, No. 12.

Koretz et al., "Model of the Accommodative Mechanism in the Human Eye", Vision Res., 1982, pp. 917-927, vol. 22.

Kasprzak, Henry, "New Approximation for the Whole Profile of the Human Crystalline Lens", Ophthal. Physiol. Opt., 2000, pp. 31-43, vol. 20, No. 1.

Martin et al., "Comparison of the Accommodation Theories of Coleman and of Helmholtz by Finite Element Simulations", Vision Research, 2005, pp. 2910-2915, vol. 45.

Pflugfelder et al., "Photogrammetric Analysis of Corneal Trephination", Arch Ophthalmol, 1992, pp. 1160-1166, vol. 110.

Rosen et al., "In Vitro Dimensions and Curvatures of Human Lenses", Vision Research, 2006, pp. 1002-1009, vol. 46.

Strenk et al., "Age-Related Changes in Human Ciliary Muscle and Lens: A Magnetic Resonance Imaging Study", IOVS, 1999, pp. 1162-1169, vol. 40, No. 6.

Strenk et al., "Magnetic Resonance Imaging Study of the Effects of Age and Accommodation on the Human Lens Cross-Sectional Area", IOVS, 2004, pp. 539-545, vol. 45, No. 2.

Weeber, et al., "On the Relationship between Lens Stiffness and Accommodative Amplitude", Experimental Eye Research, 2007, pp. 602-607, vol. 85.

\* cited by examiner

METHOD FOR CHARACTERIZING LENSES

CROSS REFERENCE

This application claims benefit of priority from U.S. Provisional Application Ser. No. 61/199,025 filed Nov. 12, 2008, the entire contents of which are incorporated by reference herein as if made part of the present specification.

FIELD OF THE INVENTION

Embodiments of the present invention relate generally to the field of lens design and lens characterization. More specifically, embodiments of the present invention relate to methods and apparatuses for developing mathematical models of the crystalline lens shape for use in modeling, description, design and production of crystalline lens and crystalline lens prosthetics.

BACKGROUND

Presbyopia and cataract are two of the most common disorders to beset human vision, especially for the aged. Presbyopia is the loss of the ability of the eye to change focus for near vision. This change is associated with a loss in the ability of the crystalline lens of the eye to change shape. The onset of presbyopia is typically around 40 to 50 years of age. When presbyopia manifests in a person, they will increasingly lose, and ultimately no longer have, the ability to attain clear vision for reading or seeing objects up close. This is currently most commonly corrected by the prescribing of reading glasses, bifocal, multifocal or aspheric progressive spectacles and contact lenses. Cataract is a disorder of the eye characterized by a loss of optical clarity of the crystalline lens. The individual with cataract will gradually lose vision in the affected eye. The current method for treating cataract is by removal of the crystalline lens (or its contents; the cortex and nucleus) and replacement of the lens with an intraocular lens (IOL) to restore correct distance focus. However, with conventional IOL implantation following cataract surgery, near vision is lost.

To overcome the problem of loss of near vision in presbyopia and post-cataract surgery, and to restore true accommodation (the ability of the eye to change continuous focus to enable near vision) some technologies have become available recently including accommodating IOL (AIOL) such as Crystalens, or Humanoptic 1 CU. Many other are currently under design and development stages. These include two-element AIOL (e.g. Synchrony by Visiogen) and other AIOLs (e.g. Nulens). A more natural strategy for restoring accommodation in the presbyope would involve, not the use of optical/mechanical devices such as those mentioned above, but the refilling of the crystalline lens with a soft material. The soft material may be refilled directly into the evacuated lens capsule (outer covering of the crystalline lens) or be refilled into a containing device such as a bladder or balloon inserted into the crystalline lens. Yet another approach to restoring accommodation is the re-softening of the hardened crystalline lens content. This may be achieved opto-mechanically by the use of, for example, lasers, or by chemical treatment Re-softening or refilling of the lens with a soft material are preferred options for restoring accommodation as the origin of presbyopia stems from a loss of softness of the content of the crystalline lens. Hence, techniques for restoring the softness of a lens would be the most direct method for restoring accommodation. There are many ways by which such approaches could be accomplished. One direct method (sometimes called "phaco ersatz"; after Parel) involves the injection of a soft gel into the capsule of the crystalline lens to replace the (removed) hardened lens content of the presbyopic eye. Another method (after Nishi) involves the implantation of a bag-like device into the capsule and then to fill the bag-like device with a soft gel. Yet another method involves the delivery of a material into the lens which can later be 'tuned' to a correct shape (after Calhoun LAL technology). Finally, a pre-formed and pre-shaped lens (after Fine) which can be thermally distorted to facilitate introduction into the lens capsule, and its original shape re-established by thermal 'plastic memory' may be used. For the latter two methods, provided the material or pre-formed lens is made of a sufficiently soft material, restoration of accommodation may be achieved.

For all of the methods mentioned above (which we hereafter call "crystalline lens prosthetics" methods), an optimum visual outcome can only be achieved if good knowledge of the shape of the natural crystalline lens as well as the most preferred optimum shape of the refilled and/or reformed lens is available.

It is an objective of the present invention to provide a method by which the surface shape (both anterior and posterior as well as near the equator) of the natural crystalline lens and the shape of a crystalline lens prosthetic can be measured, described and used for the design of optimum crystalline lens prosthetics.

Numerous analytical and finite element (FE) mechanical models of the human crystalline lens have been developed to simulate changes in lens shape during accommodation. Analytical models have been used to describe the accommodative mechanism in the human eye (Koretz and Handelman 1982) and to investigate the effects of lens elastic anisotropy on accommodation (Koretz and Handelman 1983). FE models have been used to demonstrate that Helmholtzian mechanism of accommodation is most likely for the young lens (Burd, Judge and Flavell 1999), to show that the 29 year old lens is more effective in accommodating than the 45 year old lens (Burd, Judge and Cross 2002), to compare Coleman and Helmholtzian accommodation theories (Martin, Guthoff, Terwee and Schmitz 2005), to estimate the external force acting on the lens during accommodation (Hermans, Dubbelman, van der Heijde and Heethaar 2006) and to show that the maximum zonular tension decreases with age and is the most likely cause for the decrease in accommodative amplitude with age (Abolmaali, Schachar and Le 2007). More recently FE models have been used to analyze the relationship between lens stiffness and accommodative amplitude (Weeber, van der Heijde 2007) and to determine the change in accommodative force with age (Hermans, Dubbelman, van der Heijde and Heethar 2007). FE models provide valuable information about accommodation and presbyopia. Yet, the quality of the models depends on the geometric information used to develop them. Therefore accurate geometric representation of the human crystalline lens is a critical issue for FE modeling, especially at the equatorial regions where the forces are applied.

Burd et al. (2002) and Martin et al. (2005) used geometric information recorded by Brown (1973) to develop models for lenses aged 11, 29 and 45 and therefore their studies are limited to these three ages. Hermans et al. (2006) developed their model using lens shape obtained from Scheimpflug imaging. The images contain only the central portion of the anterior and posterior surfaces of the lens. They modeled the missing regions using two conic functions. Abolmaali et al. (2007) developed their model using information from published MRI images. Their model was not age-dependent and hence is not able to take into account the changing shape and growing size of the crystalline lens, which is constantly growing in size and changing in shape throughout life. Weeber et al (2007) used geometrical information based on in-vivo measurements (Dubbelman, van der Heijde & Weeber 2005; Strenk, Semmlow, Strenk, Munoz, Gronlund-Jacob & DeMarco 1999). FE models should account for age-dependency of the lens shape and should be based on measurements of the lens shape when no stresses are applied. The isolated ex-vivo crystalline lens is not subjected to any active external forces and therefore can serve as the basis for a geometric model of a fully accommodated crystalline lens that can be used in FEM studies.

The human crystalline lens is composed of two aspherical surfaces, which have been modeled with a number of mathematical functions. The earliest eye model represents the lens as two spherical surfaces. The shape has been progressively described as hyperbolic (Howcroft and Parker 1977) parabolic (Koretz, Handelman and Brown 1984) fourth order polynomial (Strenk, Strenk, Semmlow and DeMarco 2004) and conic functions (Dubbelman, van der Hiejde 2001, Rosen, Denham, Fernandez, Borja, Ho, Manns, Parel & Augusteyn 2006). While these models present a good approximation of the human lens, they were developed for optical modeling and therefore primarily focus on the central (approximately 4 to 5 mm) region of the anterior and posterior lens surface, not providing much information about the equatorial region. Kasprzak (2000) approximated the whole profile of the human lens using a combined hyperbolic cosine and hyperbolic tangent function in polar space. This model is based on published values of radius of curvature and asphericity. This model divides the anterior and posterior lens into two 'hemispheres' and applies the mathematical function (hyperbolic cosine and hyperbolic tangent) to fit each half. The hyperbolic functions are used in polar space to ensure continuity at the lens equator. However, due to the use of two specific functions with a limited number of parameters (i.e. numerical degrees of freedom), this model cannot be guaranteed to be able to fit/describe all possible physiological crystalline lens shapes or crystalline lens prostheses. Further, due to the method of dividing the lens into an anterior and posterior half, this model can only faithfully describe those crystalline lens or prostheses which are rotationally symmetrical at the equator. Physiologically, the lens is tilted and there exists lenses which are not rotationally symmetrical at the equator. For these lenses, the model of Kasprzak would not be suitable.

It is therefore, objectives of the present invention to provide a method for numerically describing the crystalline lens shape that overcomes the disadvantages of previous models as discussed above.

SUMMARY OF THE INVENTION

According to embodiments of the present invention an age-dependent mathematical model of the crystalline lens shape has now been developed. This model overcomes the disadvantages of previous models which in particular include; insufficient degrees of freedom to be able to faithfully describe any crystalline lens or prosthesis shapes; inability to ensure continuity around the entirety of the crystalline lens and especially at the equator; and ability to describe asymmetric lens profiles. In one study we evaluated the profiles of whole isolated human lenses (n=22) aged 26 to 82, using shadow-photographs and fitting to a mathematical model involving a series of periodic functions.

A new method has been developed for mathematically describing the shape of the crystalline lens. This method overcomes disadvantages and drawbacks of previous methods as described above. This method describes the entire lens surface including anterior and posterior 'hemispheres' as well as the equatorial region as a single continuous mathematical representation, thus overcoming the problem of ensuring continuity. The method further employs a summed serial function constituting incrementally higher orders of a base function. By utilizing a sufficiently high order of base function in the summation series, any degree of accuracy of the representation may be achieved. Yet further, the inclusion of decentration terms and tilt terms provides for the description of tilted and/or asymmetric lens shapes particularly useful for describing the natural lens in situ (located physiologically, in its natural position inside the eye). Still further, the inclusion of phase parameters within the base function provides for even greater precision in describing tilted and/or asymmetrical lens shapes—especially shapes which have local asymmetry along its profile. In addition to the above, individual coefficients relating to the different order of base functions may be set to be a function of age. In this way, an age-dependent model of the lens may be constructed. The summated series function may be applied to one or more sections or meridians of a lens in order to provide a three-dimensional model.

The method of the present invention is useful in providing curve-fitting of acquired shape data to describe the shape of an individual measured crystalline lens. The acquired shape may be inputted as a direct set of surface profile coordinates within a data set, or from a direct measurement of the surface shape of the lens.

The method is also useful in describing sample or population averages of lens shapes such as may be required as an initial step in designing an intraocular lens implant that is required to also resemble a typical or average lens shape.

The method is also useful in describing an actual IOL design that is required to resemble a lens shape. Such an IOL design may be required to resemble either a typical population's lens shape, or a typical sample's (e.g. within a particular age group) lens shape, or a customized lens shape of an individual.

The series function of the present method, in a general form, is constructed from the summed series of a base function. The function is defined on a polar coordinate or spherical coordinate system for two and three dimensional representation respectively. Thus, the series function defines the radial distance from a central origin to the lens surface along a radius in a given meridian (2-D) and azimuth (3-D). The base function may be any type of function but is most preferably a periodic function (e.g. sine, cosine, etc). The base function also has the feature that an order of periodicity may be established in which each increasing order addresses different and incrementally finer details of the crystalline lens shape. The summation of a series of increasing order of the base function provides the model for the crystalline lens. In an added level of sophistication, the coefficients pertaining to different orders of the base function may themselves be defined as a function of age. In this way, an age-dependent, two or three-dimensional model of the crystalline lens may be defined by a single series function (of this model) that does not suffer discontinuity at any point.

Further objects, advantages and embodiments of the invention will become evident from the reading of the following detailed description of the invention wherein reference is made to the accompanying drawings

DESCRIPTION OF THE DRAWINGS

The file of this patent contains at least one drawing executed in color. Copies of this patent with color drawing(s)

will be provided by the Patent and Trademark Office upon request and payment of the necessary fee.

DETAILED DESCRIPTION OF THE INVENTION

Figure 2:
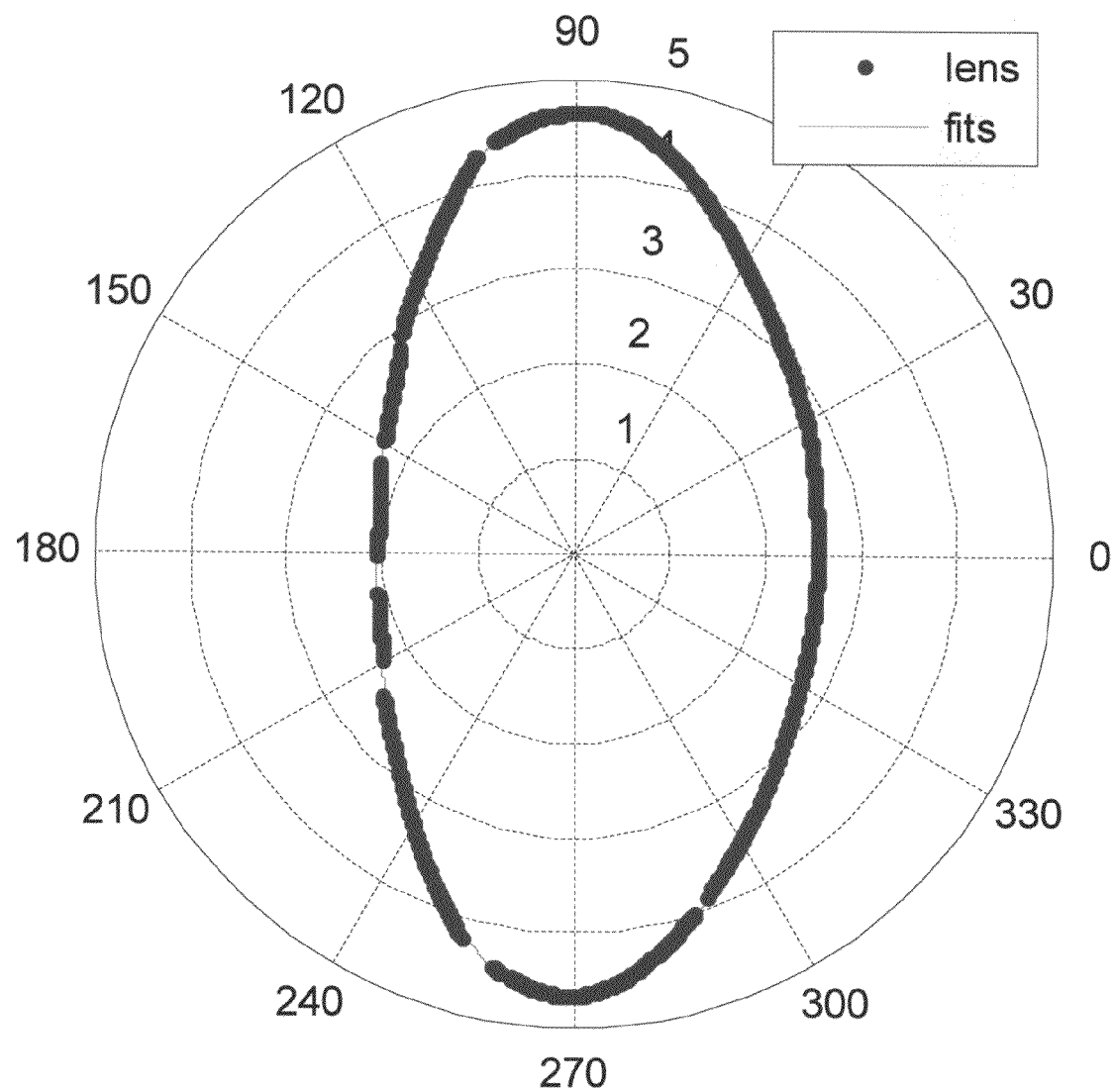
FIG. 2 is a plotted polar coordinate system showing how the series function method defines the shape of a crystalline lens without discontinuity.

The method of the present invention, called the "series function" method, is based on the summation of a series of incrementing orders of a base function. The series function is defined on a rotational coordinate system such as polar coordinates system in two-dimensions or spherical coordinates system in three-dimensions. Thus, the model provides the shape of a crystalline lens by defining the radial distance (rho) from the central origin point of the coordinate system (FIG. 2) to a given point on the lens surface as measured along any given azimuthal direction angle (theta). FIG. 2 shows the polar coordinate system of the series function method. FIG. 2 (like FIG. 4) shows a polar grid with units of radius of curvature indicated from 1 to 5. The equatorial axis of the lens is parallel to the theta=π/2 radian (90°) axis and the optical axis is parallel to the theta=0 radian (0°) axis. Positions on the lens surface are represented as coordinate pairs defining theta (angle of median) and radius (distance from central origin to surface point). Lens surface points measured from one crystalline lens are shown in the thick line while the same lens described using a series function of the present invention is shown as the thin line.

Figure 3:
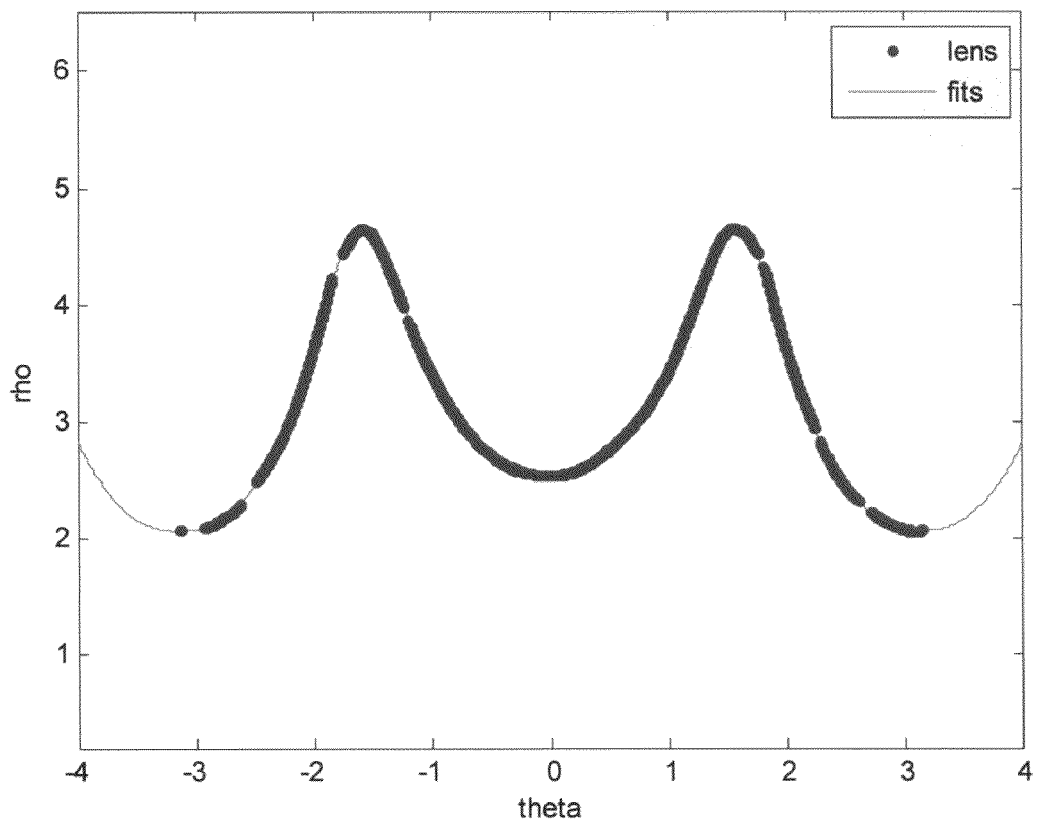
FIG. 3 is the series function method describing the same lens of FIG. 2 shown in a rectilinear radial distance (rho) versus azimuthal angle (theta) coordinate system. Such a plot is useful for evaluating the goodness-of-fit of a given series function on a given crystalline lens shape.

The entire lens shape is thus described as a set of theta-rho coordinates in two-dimensional space. An alternative method of graphing the result is to employ a rectilinear radial distance (rho) versus azimuthal angle (theta) coordinate system (FIG. 3). Therefore, FIG. 3 shows the series function method representing lens surface shape as plotted on a theta, radius rectangular coordinates system. The equatorial axis of the lens is parallel to the theta=π/2 radian (90°) axis and the optical axis is parallel to the theta=0 radian (0°) axis. Such a plot is useful for understanding the goodness-of-fit of a given series function on a given crystalline lens shape. For three-dimensional representation, a sectional meridian angle (phi) is introduced that rotationally 'sweep' the two-dimensional section around the spherical space to produce a three-dimensional lens shape description. In such a case, the lens surface is described by a set of (theta, phi, rho) coordinates.

While the base function may be any suitable function, it is most preferably a periodic function such as a cosine or sine function. The order of the function may be set arbitrarily high according to the degree of accuracy required of the model.

The most basic implementation, in 2-D, of the series function method is given in Equation 1.

$$R(\theta) = \sum_{p=0}^{i} B(\theta, p) \quad \text{(Equation 1)}$$

Where θ is the azimuthal angle in polar space, R is the radial distance from the central origin point to the lens surface in the azimuthal direction, B is the base function, p is the order of the base function and i is the highest order to be considered in the model (chosen according to level of complexity, computation time and degree of accuracy to be achieved), An exemplary usage of the method of Equation 1 is the selection of a cosine function as the base function in which case, the implementation of the series function method through Equation 1 becomes Equation 2. Note the coefficient J(p) which is an amplitude factor for each order of cosine function.

$$R(\theta) = \sum_{p=0}^{i} J(p) \cdot \cos(p \cdot \theta) \quad \text{(Equation 2)}$$

In many instances, the lens to be described may be decentered or tilted. One method for removing such asymmetry is to make use of Equations 1 or 2 after introducing decentration and rotation of the original data set (i.e. effectively shifting the central origin point and/or changing the azimuthal angle by a fixed value). This may be done using a computational/numerical method to find the optimal translation and rotation amount by, for example, minimizing the residuals (e.g. RMS) of the lens shape fitting.

An alternative method is to generalize Equation 1 by introducing an offset parameter q as shown in Equation 3. Since the value of this offset parameter varies according to the order of the base function, q is a function of p.

$$R(\theta) = \sum_{p=0}^{i} B(\theta, p, q(p)) \quad \text{(Equation 3)}$$

An exemplary usage of Equation 3 by again selecting a cosine function as the base function is shown in Equation 4.

$$R(\theta) = \sum_{p=0}^{i} J(p) \cdot \cos(p \cdot (\theta + q(p))) \quad \text{(Equation 4)}$$

It has been mentioned that the crystalline lens grows throughout life and its shape and size, therefore, changes with age. The series function model can be expanded and generalized to implicitly include an age-dependency as shown in Equation 5 (in which age is denoted by A). Again, making use of a cosine function as the base function, we can develop an exemplary model as shown in Equation 6. The relationship of coefficient J as a function of age A may be assigned any type of function from the simplest (e.g. linear or first order) to more sophisticated (e.g. logarithmic growth functions) according to the level of complexity and accuracy to be achieved.

$$R(\theta, A) = \sum_{p=0}^{i} B(\theta, p, A, q(p, A)) \quad \text{(Equation 5)}$$

$$R(\theta, A) = \sum_{p=0}^{i} J(p, A) \cdot \cos(p \cdot (\theta + q(p, A))) \quad \text{(Equation 6)}$$

Given the above equation and description, those skilled in the art should now be able to implement this method making use of other types of function for the base function. In one particular implementation, a Fourier-decomposition (analysis) type approach may be used to generate the series function model.

The series function method may be embedded into a device suitable for modeling the shape of crystalline lens, designing and optimizing crystalline lens prosthetics as well as facilitating or effecting the fabrication and manufacture of crystalline lens prosthetics. Such a device should consist of three modules; an input module, a processing module and an output module.

The input module may consist of hardware and/or software designed for acquiring data from a data source of crystalline lens or prosthetic shape. Such data source may be inputted directly by manual data entry, or electronically by electronic data entry or electronic data transfer or exchange from another device (particularly a device for measurement lens shape) or data store or file system (such as object linking and embedding or OLE, open database connectivity or ODBC). The input module may also directly acquire data pertaining to lens shape by including within its module, hardware and/or software systems for the direct or indirect measurement of crystalline lens shape, including optical coherence tomography (OCT), ultrasonography, profilometry and combinations thereof.

The processing module is the main computation module of the device. It would comprise algorithms and hardware and/or software facilities for implementing the series function method of the present invention.

The output module of the device would be responsible for outputting the lens profile model. It would comprise algorithms and hardware and/or software facilities for outputting mathematical lens profile description (e.g. a set of coefficients). Such an output would typically be destined to a lens profile description receptacle for further activities including graphic description (e.g. a camera, animation generator, or plotter), or lens fabrication or manufacture (e.g. by direct computer-assisted design CAD and manufacture CAM). The output may also be transferred by direct manual data output, or by electronic data output including electronic data transfer or exchange to another device by e.g. OLE or OBDC calls.

Herein we provide detailed examples of the series function model of the whole crystalline lens. Examples given below are based on measurements obtained from shadow photographs of 22 lenses ranging in age from 26 to 82.

EXAMPLES

The next two sections describe a procedure by which the crystalline lens may be prepared so geometrical data relating to shape may be obtained. This is provided as an example of how such preparation and data may be conducted. Given the following description, the individuals skilled in the art should then be able to identify other methods by which lens samples may be prepared and geometrical data obtained.

Lens Preparation

All human eyes were obtained and used in compliance with the guidelines of the Declaration of Helsinki for research involving the use of human tissue. The 22 crystalline lenses used in this study were from whole, intact cadaver eyes, in the age range of 26 to 82, obtained from American Eye Banks. The postmortem time varied from 1 to 5 days, during which time the whole eyes (globes) were stored at 2-6° C. in sealed jars on a bed of gauze, moistened with saline. Ophthalmic surgeons removed the cornea and iris using an operating microscope. The lens was extracted by carefully cutting the zonules and adherent vitreous using Vannas scissors. Wire lens spoons (Segal Instruments, Bombay, India) were used to immediately place the lens on the sutures of the testing cell, which was pre-filled with a DMEM solution (Augusteyn, Rosen, Borja, Ziebarth, & Parel, 2006). The time from lens extraction to measurement was approximately 6 minutes. Lens capsule integrity was visually inspected using the optical comparator (Rosen et al. 2006). Torn capsules usually appeared as surface irregularities or small flaps of tissue protruding from the capsule surface. Images of 94 human crystalline lenses were available. Of these, 29 lenses were excluded due to a capsule tear or cataractous changes and 43 lenses were excluded because they exhibited capsular separation, leaving 22 lenses for this study.

Shadow Photogrammetry

Figure 1:
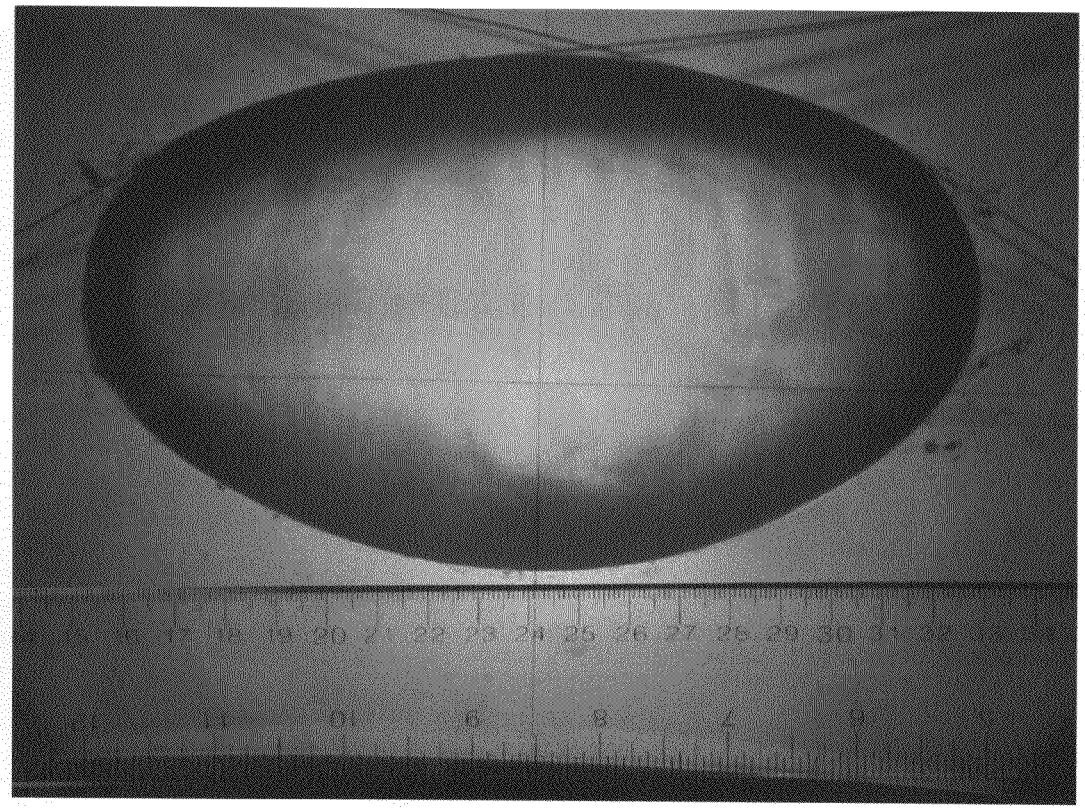
FIG. 1 is a shadow-photograph showing one two-dimensional section of a human crystalline lens. The shape and size of a crystalline lens is individual and changes throughout life.

The technique of shadow photogrammetry of eye tissues has been described in detail in earlier publications (Denham, Holland, Mandelbaum, Pflugfelder & Parel, 1989; Pflugfelder, Roussel, Denham, Feuer, Mandelbaum & Parel, 1992; Rosen et al. 2006; Augusteyn et al, 2006). A modified optical comparator (BP-30S, Topcon, Tokyo, Japan) projects a 20× magnified shadow of an excised lens onto a viewing screen. Two light sources, one for retro-illumination and the other for sagittal illumination, enable photography of the lens in the coronal and sagittal views. The immersion cell described in Rosen et al. (2006) was modified by replacing the lens-holding ring with a supporting mesh made of 10-0 nylon sutures. This enabled the entire posterior surface of the lens to be available for contour detection (FIG. 1). A 4.0 Mp Nikon Coolpix 4500 digital camera (Tokyo, Japan) was used to capture the coronal and sagittal views of the lens. A ruler was also photographed on the same images for scaling purposes.

Image Analysis

The images were preprocessed with Canvas 9.0 (ACD Systems of America, Miami, Fla.). They were scaled against the ruler included in the image and were adjusted for magnification (20×) of the comparator. The images were then cropped to remove the ruler. The preprocessed images were loaded into Matlab (Mathworks, Inc., Natick Mass.) and converted to grayscale. An algorithm composed of two separate processes was used to detect the lens-contour. The first process detected a thick approximate contour of the lens, using the Prewitt edge detector and morphological functions. This eliminated false edges generated by the sutures and lens material. The second separate process used the Canny edge detector, to detect a fine contour of the lens. An intersection of the outputs of the two processes produces the lens contour with minimal false contours. A few false contours that were detected were removed manually. For the majority of the images, the size of each pixel in the plane of the lens was between 4 and 5 μm.

From the foregoing, a set of coordinate pairs in Cartesian space describing the profile of the lens becomes available. Such a data set may consist of n number of data points in 2D Cartesian space in which the data points are described by coordinate pairs e.g. $\{X_i, Y_i; i=0 \ldots n\}$.

Such a data set represents a set of measured/digitized points describing the surface profile of an entire crystalline lens including anterior, posterior and equatorial surfaces.

In order to prepare the data set for modeling with the series function method of the present invention, the coordinate pairs need to be transposed to a polar or spherical coordinate system. Firstly, a translation is applied with the center origin of the polar system defined to be located at $\{x_c, y_c\}$ thus the new coordinate pairs $\{X_i', Y_i', i=0 \ldots n\}$ becomes $$X_i' = X_i - x_c \quad \text{(Equation E1a)}$$

$$Y_i' = Y_i - y_c \quad \text{(Equation E1b)}$$

This translation provides the degree of freedom useful for varying the centre of the polar coordinate system to minimize RMS during fitting of a series function model.

Next, the translated data points are converted to polar space with the centre of polar system located at $\{x_c, y_c\}$ and data points described by polar coordinate pairs $\{\theta i; ri, i=0 \ldots n\}$ where $$\theta_i = \tan^{-1}(X_i'^2/Y_i'^2) \quad \text{(Equation E2a)}$$

$$r_i = \sqrt{X_i'^2 - Y_i'^2} \quad \text{(Equation E2b)}$$

For this particular example, the polar coordinate system used defines 0° azimuthal angle as equivalent to the positive y-axis direction of the Cartesian coordinates system and is nominally coincident with the axis of the crystalline lens (as in FIG. 1). This provides the basis for employing cosine terms which are symmetric about the lens axis. FIG. 1 shows a shadow photograph of a human crystalline lens, photographed with a ruler for scaling purposes.

Finally, the polar system may be tilted about centre with new azimuthal direction at $\theta_t$ from original. The data points coordinates are rotated in polar space to the new tilted polar system with rotated data points described by new polar coordinate pairs $\{\theta_i', r_i'; i=0 \ldots n\}$ where $$\theta_i' = \theta_i - \theta_t \quad \text{(Equation E3a)}$$

$$r_i' = r_i \quad \text{(Equation E3b)}$$

This rotation provides the degree of freedom useful for finding a vertical axis of symmetry of the data set by minimizing RMS for fitted symmetric cosine terms.

Modeling with the Series Function Method: Example Using Cosine as Base Function.

Define a series function employing cosine function as the base function. The cosine series has terms of order m as a model to predict the radial distance $r_i'$ for each given meridional angle $\theta_i'$ with predicted radial distance $R_i'$ given by $$R_i' = \sum_{j=0}^{m} A_j \cdot \cos(j \cdot \theta_i') \quad \text{(Equation E4)}$$

Numerical Solution and Error Function:

The values for the coefficients of Equation E4 above may be found by numerical (e.g. least squares) techniques. This is facilitated by constructing an error function EF based on the RMS of the residual of prediction of radial distance $r_i'$ where $$EF = \sqrt{\frac{\sum_{i=1}^{n}(r_i' - R_i')^2}{n}} \quad \text{(Equation E5)}$$

Fitting of Model to Data Set:

The model defined above can be fitted to the data by minimizing the error function using an iterative convergence algorithm as understood by those skilled in the art.

The variables providing the degrees of freedom of model fitting are $\theta_t$=tilt of the axis of symmetry of data set relative to coordinate system $x_c$ and $y_c$=centre of polar coordinate system relative to Cartesian system $A_j$=amplitude (coefficient) of $j^{th}$ order cosine term.

Figure 7A:
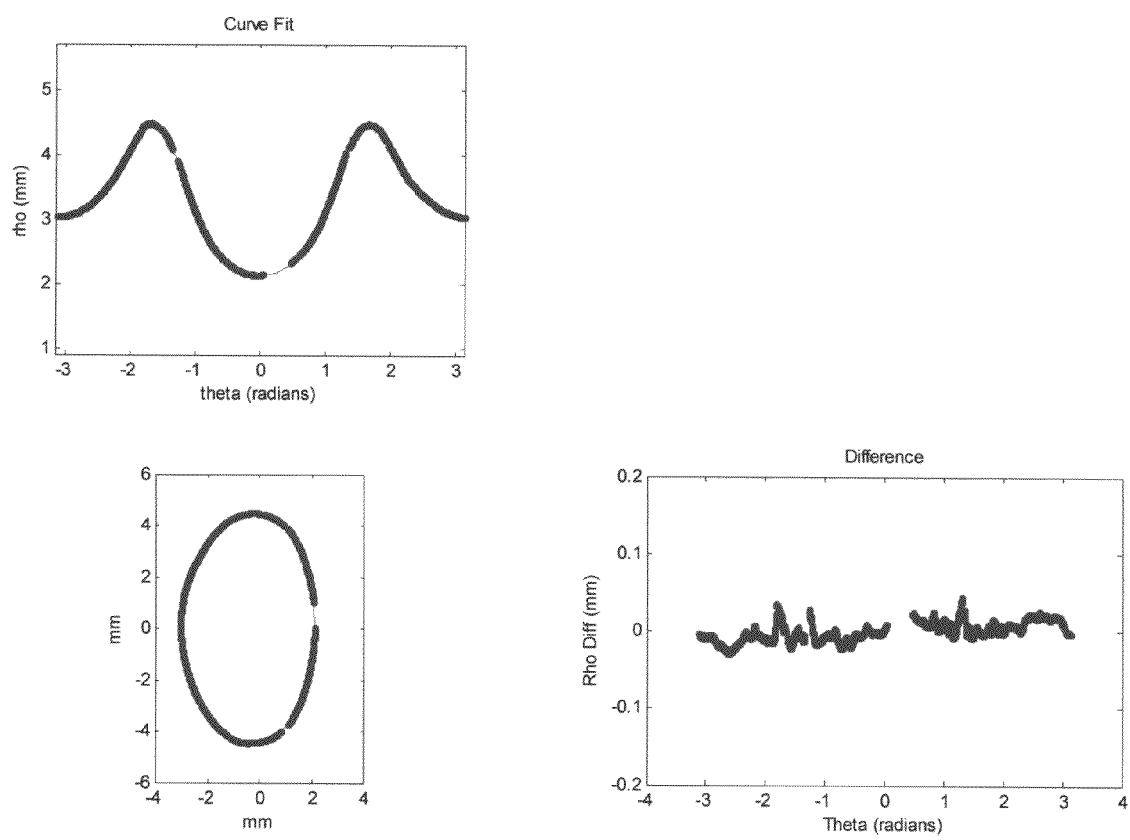
FIGS. 7a-c are exemplary plots of Curve Fitting Method on different crystalline lenses. Each group of three graphs show (top left) a plot of radial distance (rho) versus angle (theta), x-y plot of radial versus axial distance (bottom left) and residual error after fitting (bottom right).
Figure 7B:
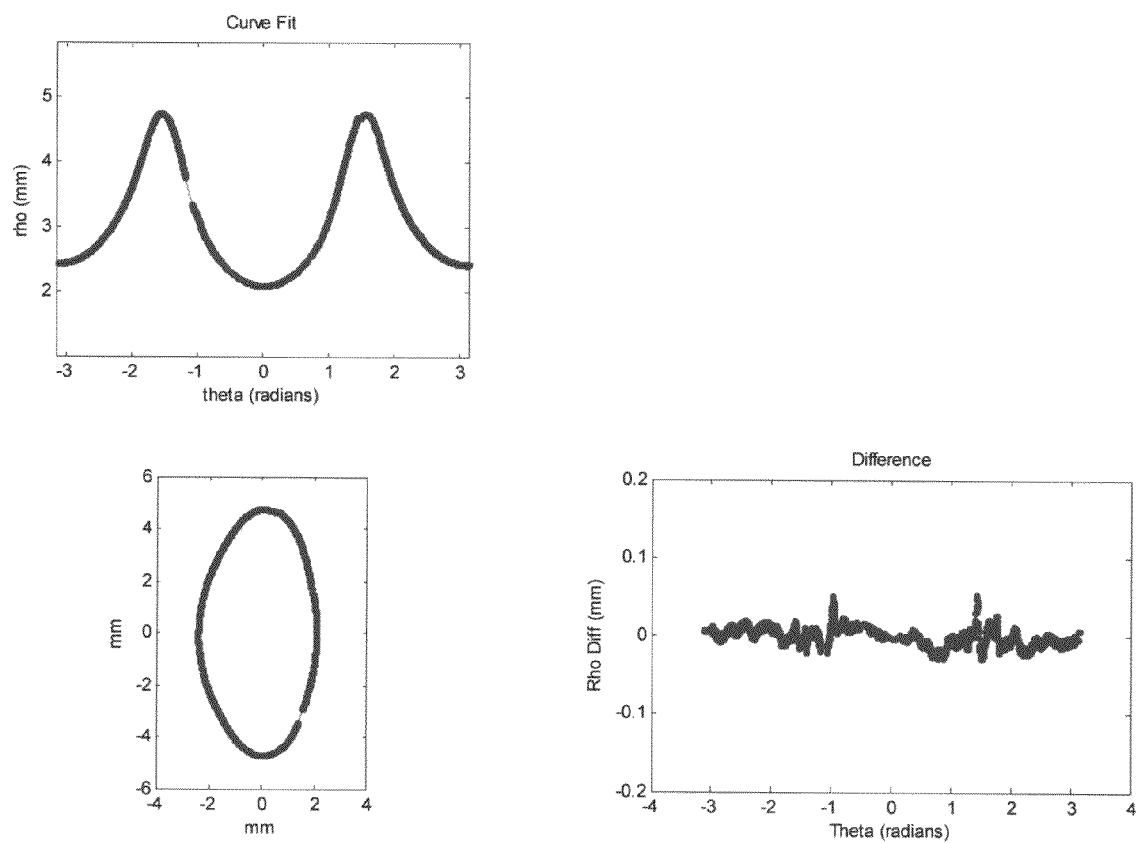
Figure 7C:
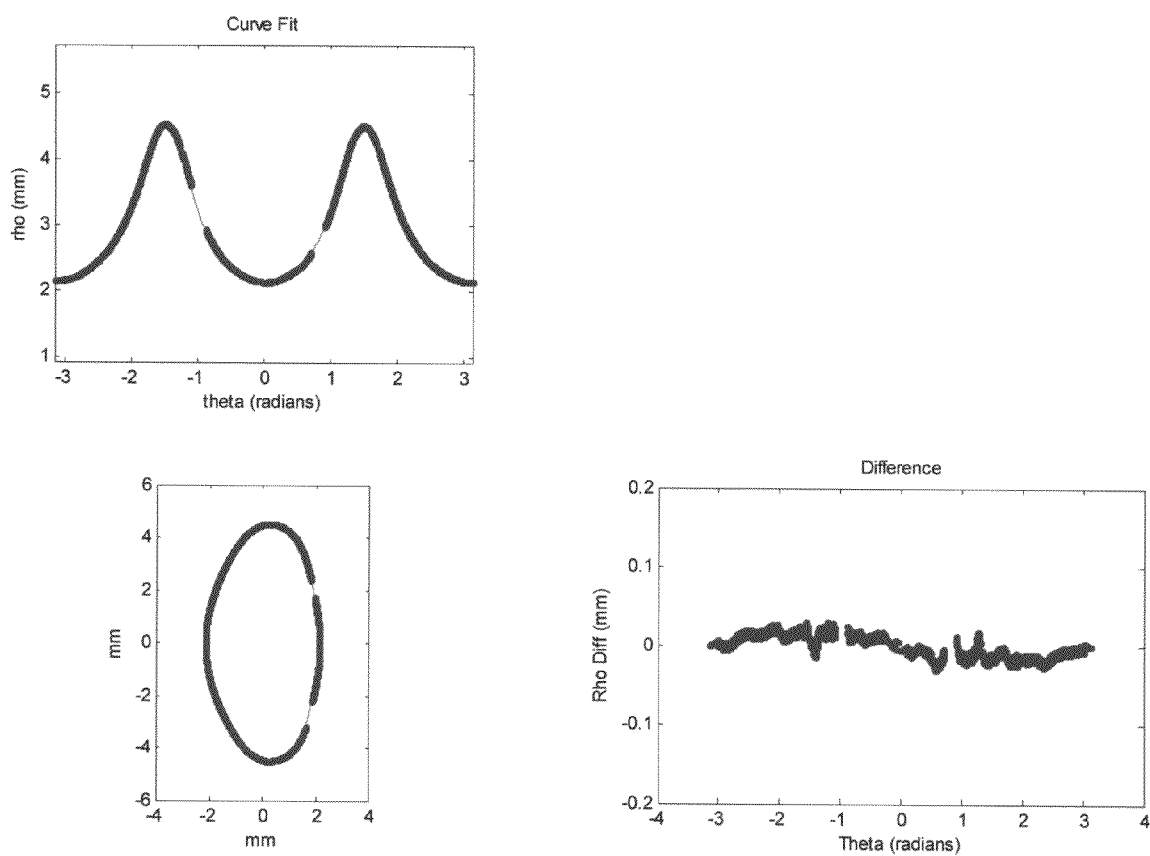

The lens profile, derived and described using the cosine series function method with value found by a computational, iterative numerical solution (least squares) technique, described above, of 22 human lenses ranging in age from 26 to 82 years are given in the following section. Exemplary plots using this method (called the "Curve Fitting Method") on a few different crystalline lenses are given in FIGS. 7a to 7c. In these figures, each group of three graphs show (in the top left graph) a plot of radial distance (rho) versus angle (theta), x-y plot of radial versus axial distance (in the bottom left graph) and residual error after fitting (in the bottom right graph).

Fourier Decomposition Technique

An alternative method by which to derive the values of the coefficients of the foregoing series function (using cosine base function) is by the Fourier-decomposition technique (FDM). By way of example, one way by which Fourier-decomposition may be applied to the data set involves first performing a cubic interpolation on the lens profile to obtain a curve with a sampling interval of approximately, 0.0001 radians. The curve may then be decomposed with Equation E6, where N is the sampling interval.

$$a_n = \left(\frac{2}{\pi} \sum_{\theta=-\pi}^{\pi} r(\theta)\cos(n\theta)\right) \frac{N}{2} \quad \text{(Equation E6)}$$

Figure 8A:
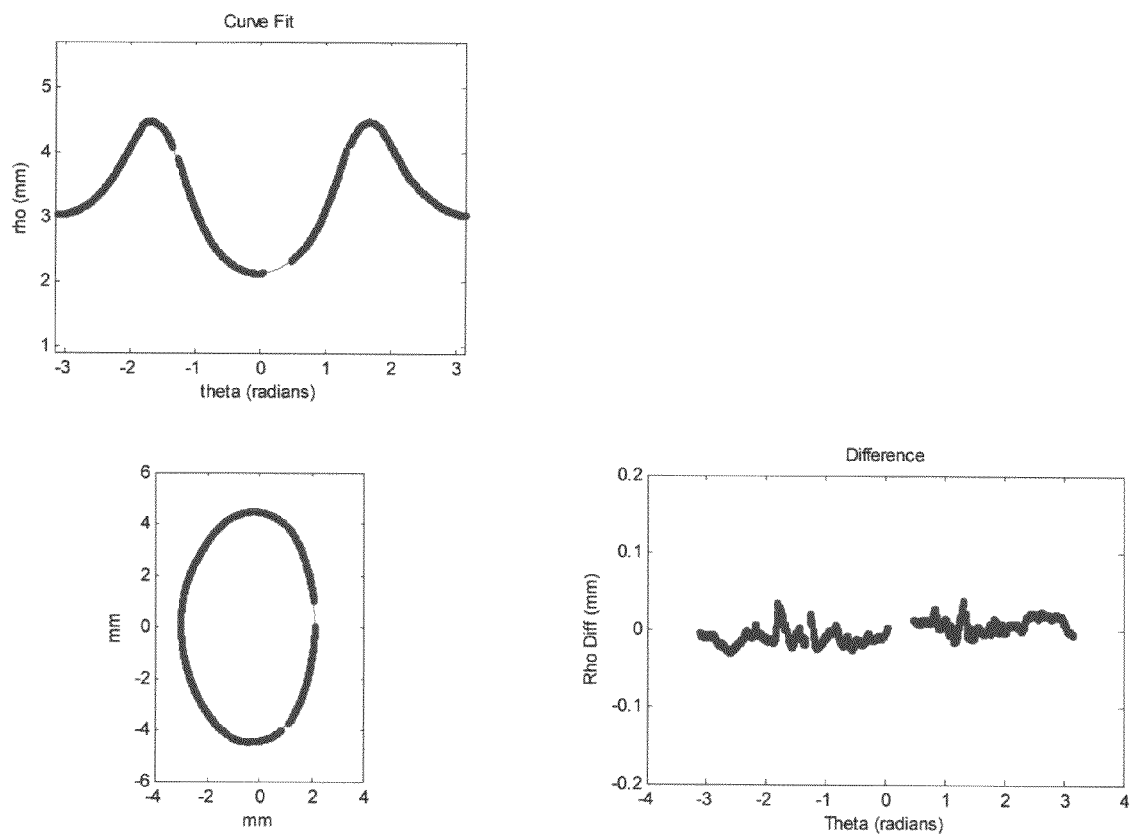
FIGS. 8a-c are exemplary plots from Fourier Decomposition Method on different crystalline lenses. Each group of three graphs show a plot of rho radial distance versus theta angle (top left), x-y plot of radial versus axial distance (bottom left) and residual error after fitting (bottom right).
Figure 8B:
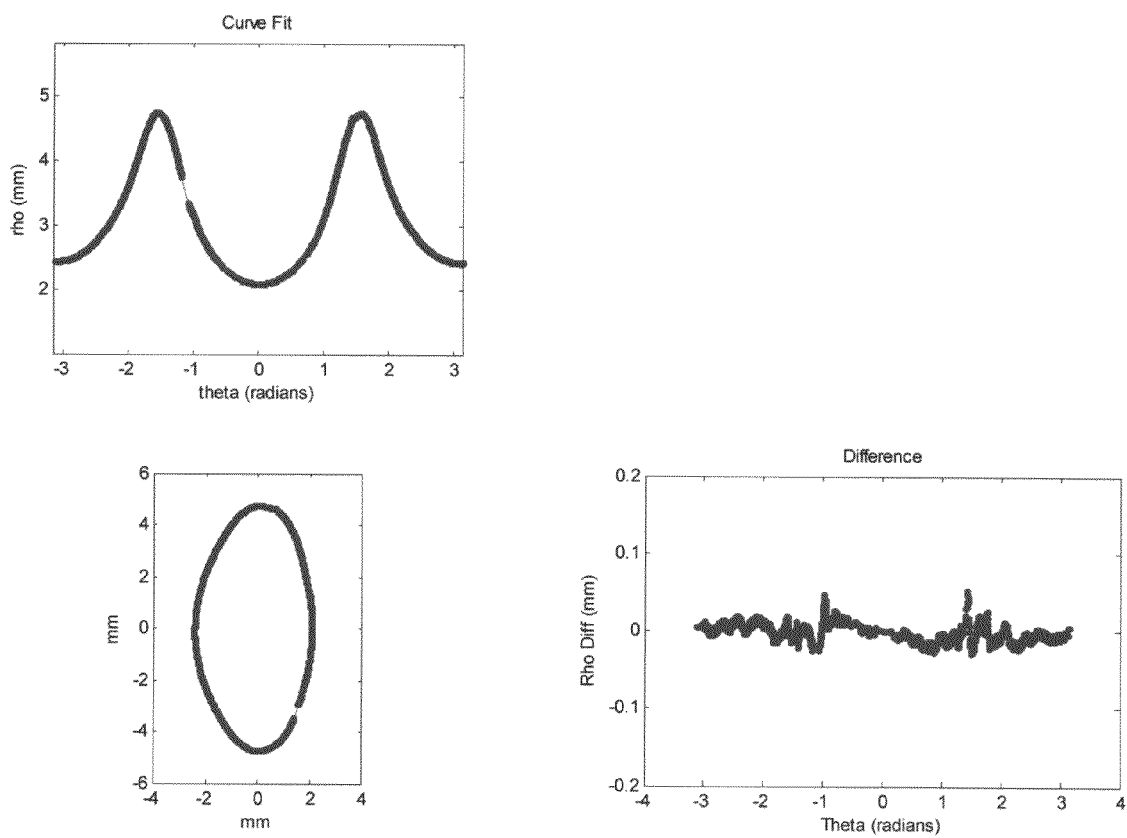
Figure 8C:
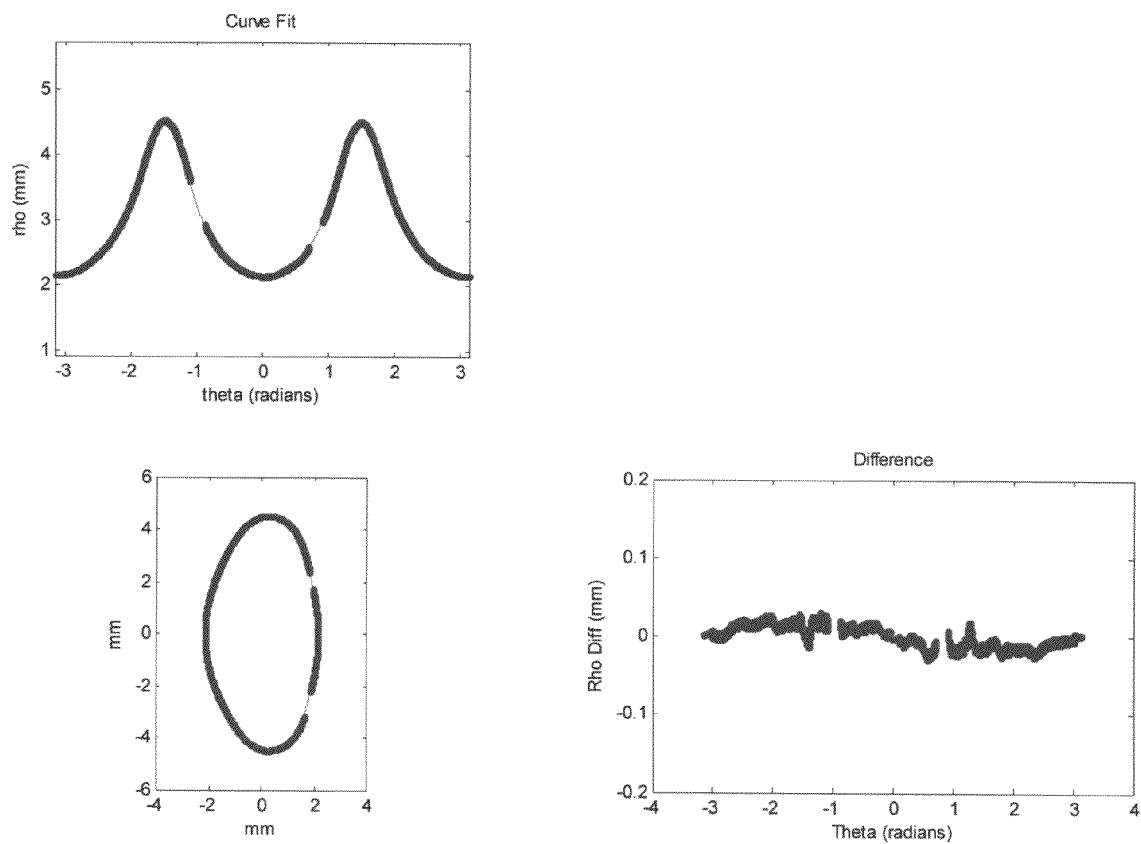

The lens profile, derived and described using the cosine series function method with value found by the Fourier-decomposition technique, of 22 human lenses ranging in age from 26 to 82 years are given in the following section. Exemplary plots using this method (called the "Fourier Decomposition Method") on a few different crystalline lenses are given in FIGS. 8a to 8c. In these figures, each group of three graphs show (in the top left graph) a plot of radial distance (rho) versus angle (theta), x-y plot of radial versus axial distance (in the bottom left graph) and residual error after fitting (in the bottom right graph).

Number of Orders and Accuracy

Figure 6:
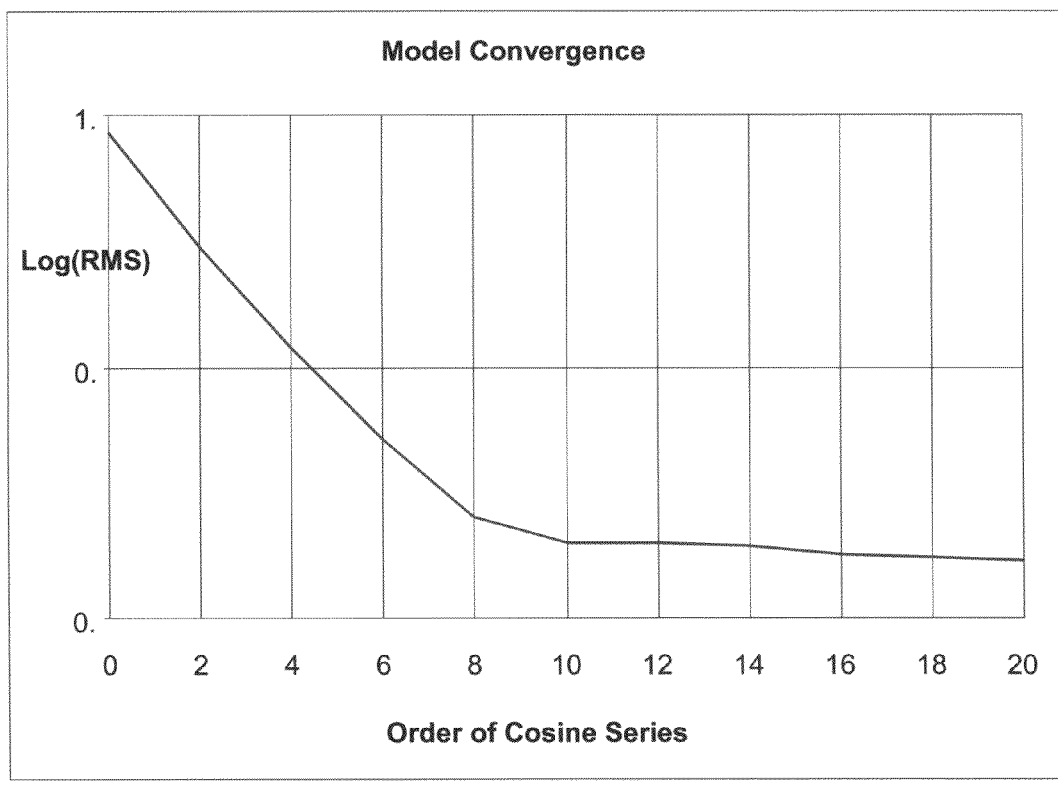
FIG. 6 is a graph showing increasing accuracy of curve fitting with increasing number of orders of the base function. For practical purposes, reasonably good accuracy relative to computational efficiency can be achieved with around 8 to 10 orders.

The graph of FIG. 6 shows that with greater number of orders of the base function, greater degrees of accuracy for representing the lens profile may be achieved. In the graph, as the order of the series increase, the RMS of the numerical fit of the lens shape decreases. While accuracy continues to increase with increasing number of orders chosen, it can also be seen that much of the improvement in accuracy occurs, in the case of using cosine function as the base function, at orders below 10.

Example Results of Lens Profile Using Series Function Model

Figure 9:
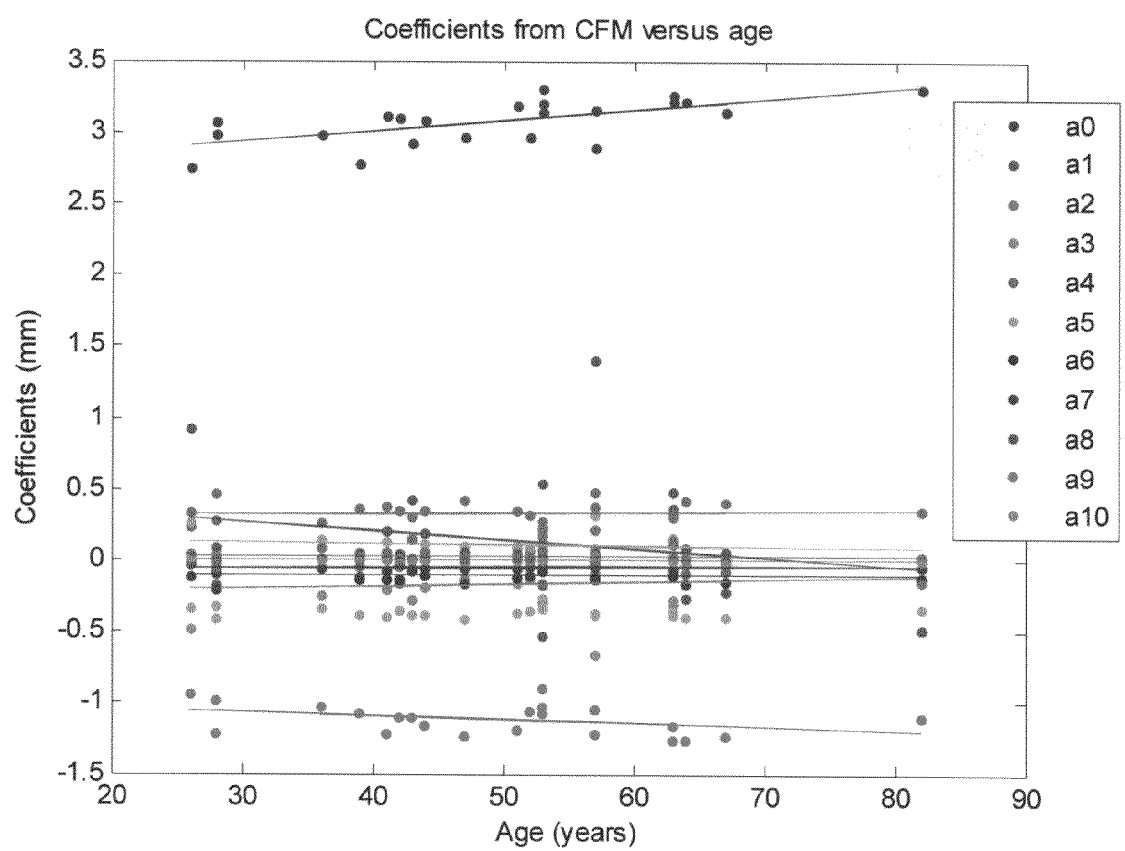
FIG. 9 is a graph showing the age-dependency of coefficients obtained from on a sample of crystalline lenses using the Curve Fit Method.
Figure 10:
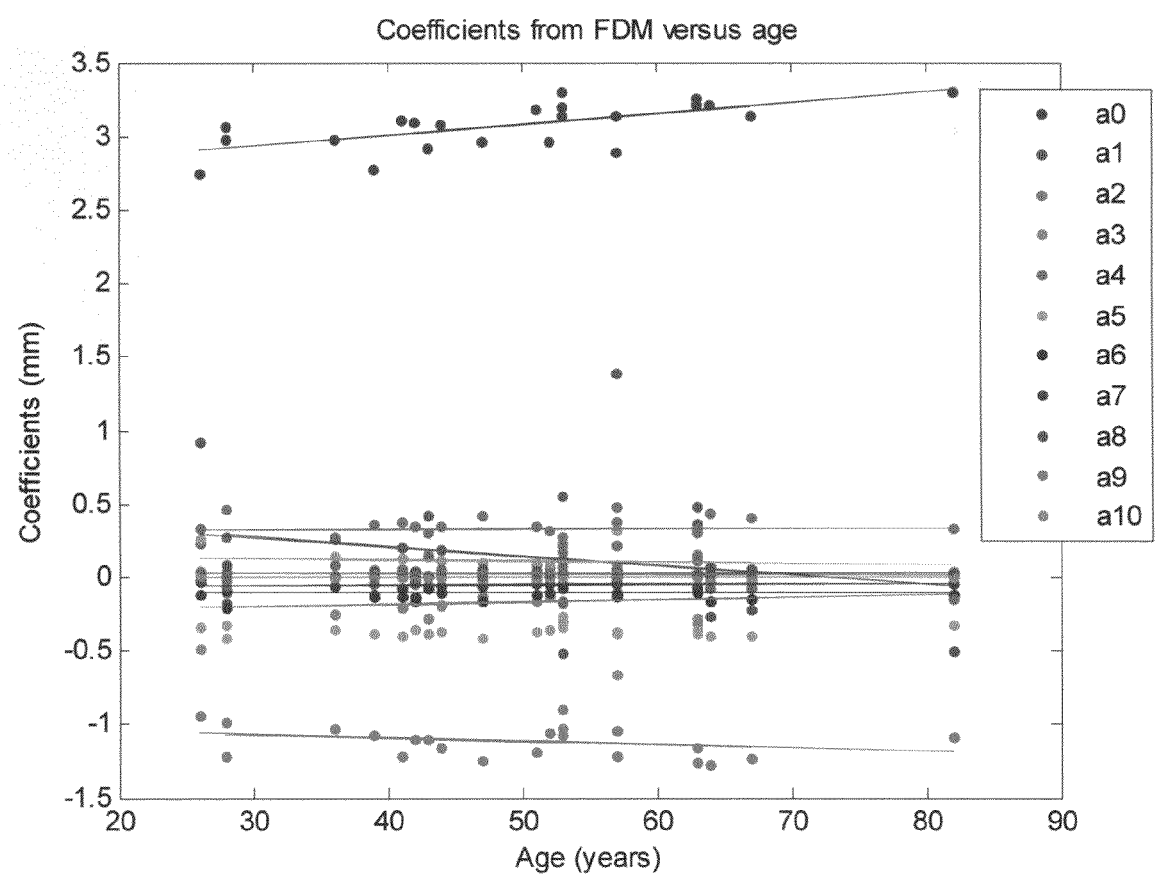
FIG. 10 is a graph showing the age-dependency of coefficients obtained from a sample of crystalline lenses using the Fourier Decomposition Method.

From our studies with a large number of lenses from eyes and donors of different ages, we discovered a clear age-dependency in some of the coefficients in the Series Function Model. Examples of the age-dependency of the coefficients obtained from the two methods are presented in FIGS. 9 (for the Curve Fit method) and 10 (for the Fourier Decomposition method). Results illustrating the age-dependency of the coefficients from $0^{th}$ to $10^{th}$ order are given in Table 1 for the Curve Fit method and Table 2 for the Fourier Decomposition method.

The $1^{st}$ coefficient $a_0$ was a coefficient whose slope exhibited a significant trend with age, for both methods. Linear regression of data obtained from the 22 lenses was performed to determine age dependent changes in the equatorial diameter (D), sagittal thickness (T), posterior sagittal thickness (bP) and anterior sagittal thickness (bA) (FIG. 2 and FIG. 3). All dimensions increased with age. Bland Altman analysis was performed to compare values obtained from the two methods. The CFM estimated higher values for the anterior thickness and diameter of the lens, and lower values for the posterior thickness. The total thickness of the lens was almost the same for both methods.

Figure 4:
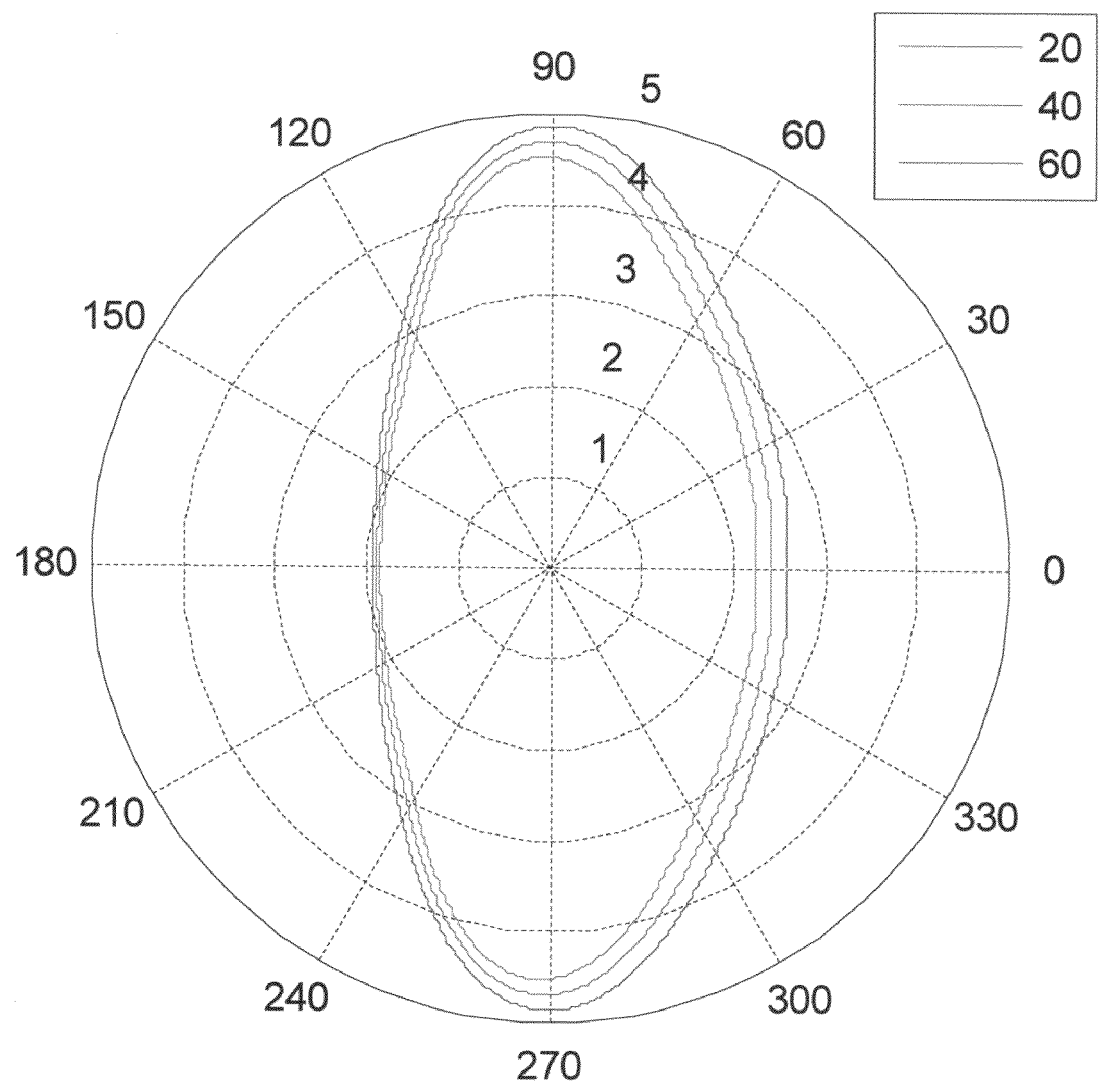
FIG. 4 shows graphs in a polar coordinate system showing the age-related changes in lens shape as depicted by the age-dependent series function method. The predicted shape of a 20 (inner-most curve), 40 and 60 (outer-most curve) year old lens is shown.
Figure 5:
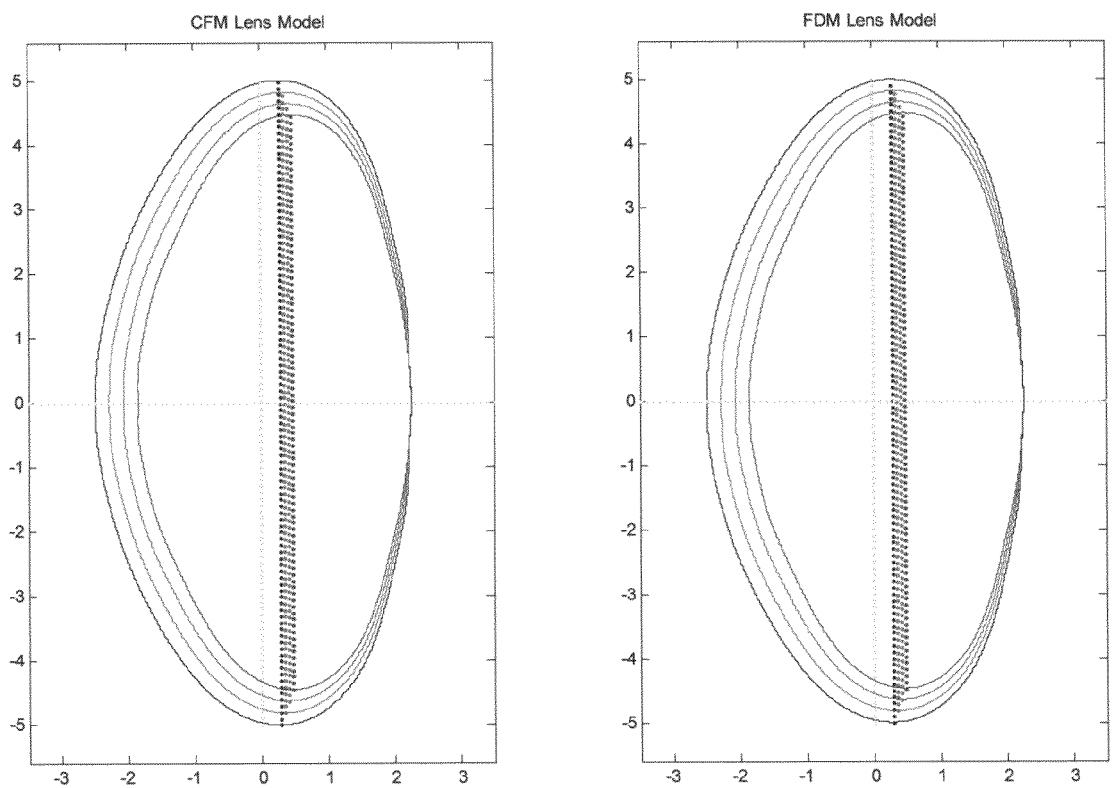
FIG. 5 shows the age-dependent lens shape for 20, 40, 60 and 80 year old lenses. The inner-most curve is the 20 year old while the outer-most curve is the 80 year old. The graph on the left shows the CFM model and the figure on the right shows the FDM model. The vertical lines represent the equators of the lenses.

The age-dependent lens shape from modeling using the two methods, for 20, 40, 60 and 80 year old lenses is presented in FIGS. 4 and 5. The results are summarized in Tables 3 and 4. According to these models, the equator, or the diameter of the lens, is not located at the center of the model and it moves away from the anterior capsule and towards the center of the model with age.

However, the relationship between some coefficients or parameters and age (Tables to 7) provides a method by which lens description, or prosthetic design, may be parameterized according to the age of the patient. For example, where individual lens profile data is not available (e.g. traumatic cases in which the lens has luxated or disrupted and hence not available for measurement), population averages including consideration for the age-related dependency of the coefficients can be used to design the appropriate prosthetic per the above-mentioned fitting method and age-dependent results.

Cross-Sectional Area, Volume and Surface Area

From our studies, we found that lens parameters such as cross-sectional area, volume and surface area increased significantly with age (Tables 5, 6 and 7).

TABLE 1

Age-dependency of coefficients obtained from fitting lens shapes using the Curve Fitting method.

| Co-efficient | A (Offset) (mm) | Error (mm) | p value | B (Slope) (mm/year) | Error (mm) | p value |
|---|---|---|---|---|---|---|
| a0 | 2.70913 | 0.0969 | <.0001 | 0.00742 | 0.0019 | 0.0008 |
| a1 | 0.46106 | 0.3569 | 0.2112 | -0.0064 | 0.007 | 0.368 |
| a2 | -0.98742 | 0.0828 | <.0001 | -0.00257 | 0.0016 | 0.1273 |
| a3 | -0.25155 | 0.1389 | 0.0852 | 0.0016 | 0.0027 | 0.5609 |
| a4 | 0.30123 | 0.0584 | <.0001 | 0.00056 | 0.0011 | 0.6282 |
| a5 | 0.14891 | 0.0605 | 0.0231 | -0.00083 | 0.0012 | 0.4918 |
| a6 | -0.09588 | 0.0393 | 0.0242 | -0.00013 | 0.0008 | 0.8677 |
| a7 | -0.06835 | 0.025 | 0.0129 | 0.00029 | 0.0005 | 0.5552 |
| a8 | 0.02597 | 0.0235 | 0.2821 | 0.00002 | 0.0005 | 0.9666 |
| a9 | 0.02474 | 0.0098 | 0.02 | -0.00003 | 0.0002 | 0.8769 |
| a10 | -0.00814 | 0.0131 | 0.5411 | 0.0001 | 0.0003 | 0.7106 |

TABLE 2

Age-dependency of coefficients obtained from fitting lens shapes using the Fourier Decomposition method.

| Co-efficient | A (Offset) (mm) | Error (mm) | p value | B (Slope) (mm/year) | Error (mm/year) | p value |
|---|---|---|---|---|---|---|
| a0 | 2.71071 | 0.0971 | <.0001 | 0.0074 | 0.0019 | 0.0009 |
| a1 | 0.46558 | 0.3568 | 0.2067 | -0.00649 | 0.007 | 0.3618 |
| a2 | -0.99445 | 0.084 | <.0001 | -0.00241 | 0.0016 | 0.1563 |
| a3 | -0.2525 | 0.1386 | 0.0835 | 0.0016 | 0.0027 | 0.56 |
| a4 | 0.30898 | 0.0582 | <.0001 | 0.0004 | 0.0011 | 0.7305 |
| a5 | 0.1458 | 0.0597 | 0.0241 | -0.00074 | 0.0012 | 0.5334 |
| a6 | -0.09743 | 0.0389 | 0.0209 | -0.00009 | 0.0008 | 0.9083 |
| a7 | -0.07028 | 0.0244 | 0.0092 | 0.00033 | 0.0005 | 0.5018 |
| a8 | 0.02623 | 0.0226 | 0.2585 | -0.00001 | 0.0004 | 0.9904 |
| a9 | 0.02378 | 0.0086 | 0.0118 | -0.00006 | 0.0002 | 0.7339 |
| a10 | -0.00833 | 0.0114 | 0.4723 | 0.00009 | 0.0002 | 0.6833 |

TABLE 3

Linear regression of the dimensions from CFM. The equation is dimension = A + B × age (mm).
Dimensions from CFM

| Dimension | Offset (A) (mm) | Error (mm) | p value | Slope (B) (mm/year) | Error (mm/year) | p value |
|---|---|---|---|---|---|---|
| bP | 1.6301 | 0.3222 | 0.0001 | 0.01077 | 0.0063 | 0.1016 |
| bA | 2.25969 | 0.2391 | <.0001 | 0.00003 | 0.0047 | 0.9942 |
| T | 3.8898 | 0.2102 | <.0001 | 0.0108 | 0.0041 | 0.0158 |
| D | 8.25561 | 0.4704 | <.0001 | 0.0212 | 0.0092 | 0.0315 |

TABLE 4

Linear regression of the dimensions from FDM. The equation is
dimension = A + B × age (mm).
Dimensions from FDM

| Dimension | Offset (A) (mm) | Error (mm) | p value | Slope (B) (mm/year) | Error (mm/year) | p value |
|---|---|---|---|---|---|---|
| bP | 1.63334 | 0.3219 | 0.0001 | 0.01074 | 0.0063 | 0.1024 |
| bA | 2.25811 | 0.2378 | <.0001 | 0.00002 | 0.0046 | 0.996 |
| T | 3.89132 | 0.2117 | <.0001 | 0.01076 | 0.0041 | 0.0168 |
| D | 8.29214 | 0.468 | <.0001 | 0.02039 | 0.0091 | 0.0369 |

TABLE 5

Linear regression of the Cross-Sectional Area obtained from
CFM and FDM. CSA = A + B × age ($mm^2$).
Cross-Sectional Area

| | Offset (A) ($mm^2$) | Error ($mm^2$) | p value | Slope (B) ($mm^2$/year) | Error ($mm^2$/year) | p value |
|---|---|---|---|---|---|---|
| CFM | 24.7954 | 1.5988 | <0.0001 | 0.15414 | 0.0311 | 0.0001 |
| FDM | 24.85133 | 1.6014 | <0.0001 | 0.15308 | 0.0312 | 0.0001 |

TABLE 6

Linear regression of the Volume obtained from CFM and FDM.
V = A + B × age ($mm^3$).
Volume

| | Offset (A) ($mm^3$) | Error ($mm^3$) | p value | Slope (B) ($mm^3$/year) | Error ($mm^3$/year) | p value |
|---|---|---|---|---|---|---|
| CFM | 136.2328 | 13.838 | <0.0001 | 1.397 | 0.2696 | <0.0001 |
| FDM | 137.3042 | 13.9114 | <0.0001 | 1.3745 | 0.271 | 0.0001 |

TABLE 7

Linear regression of the Surface Area obtained from CFM and FDM.
SA = A + B × age ($mm^2$).
Surface Area

| | Offset (A) ($mm^2$) | Error ($mm^2$) | p value | Slope (B) ($mm^2$/year) | Error ($mm^2$/year) | p value |
|---|---|---|---|---|---|---|
| CFM | 151.5254 | 10.1598 | <0.0001 | 0.8022 | 0.1979 | 0.0006 |
| FDM | 152.5218 | 10.1833 | <0.0001 | 0.7795 | 0.1984 | 0.0008 |

The above sections presented the series function model of the present invention that describes the shape of the whole lens with a single mathematical equation. The models are obtained by two methods—least squares numerical solutions, and Fourier decomposition. The Fourier decomposition technique may be preferred to that of the computational/least squares method as the values of the coefficients remain unchanged when additional orders of the base function are added to the series.

While cosine function was used as the base function, it should now be appreciated by those skilled in the art that other function types may be used as base function.

For utility, the above algorithm and method may be implemented in a device consisting of a number of modules. Three distinct functional modules are deemed essential. These modules are responsible for the inputting of data (input module) into the algorithm, a module which implements the algorithm of the present invention (processing module), and a module for outputting the calculated description of the lens or prosthetic (output module).

The input module would comprise algorithms and hardware or software facilities for acquiring lens profile data from a data source. For example, via manual data-entry, electronic data transfer or data exchange from another device such as a computer. Other possibilities include object linking and embedding (OLE) methods and open database connectivity (ODBC) common to many computer data exchange protocols. The input module may also be integral to a device for direct biometric measurement of crystalline lens such as optical coherence tomography (OCT), and profilometry.

The processing module will house the computation engine (hardware or software facilities) necessary for carrying out the algorithms and for implementing the method of this invention.

The output module provides the results of the processing module in a format useful to the end-user (whether individual or device). It will consist of hardware and software for outputting mathematical lens profile description in a format compatible with the receiver of the data. This may include hardcopy printouts, electronic data transfer or exchange to another device, object linking and embedding (OLE), open database connectivity (ODBC). Other possibilities include the direct connection from the output module to a device for direct output of crystalline lens or prosthetic shape, such as computer assisted design and manufacturing (CAD or CAM) devices such as lathes, mills, cameras and plotters. The output module (or entire device) may, in sophisticated implementations, be integral to such design and manufacturing machineries.

The invention may be embodied in other specific forms without departing from the spirit or essential characteristics thereof. The present embodiments are therefore to be construed in all respects as illustrative and not restrictive, the scope of the invention being indicated by the claims set forth below rather than by the foregoing description. All modifications which come within the meaning and range of equivalency of the claims are therefore intended to be embraced therein.

The invention claimed is:

1. A lens system for facilitating the description of a lens design or quantitative description of a lens comprising:
   hardware providing:
      an input module;
      a processing module; and
      an output module;
   wherein said input module comprises algorithms for acquiring lens profile data from a data source, and said processing module comprises algorithms for implementing a method for describing the shape of a lens, and said output module comprises algorithms for outputting a mathematical lens profile description to a lens profile description receptacle, and an output device for direct output of lens shape; wherein the algorithm comprise:
   a definition of a mathematical series function consisting of a mathematically summed series of a number of orders of a mathematical base function; and
   facilities to fit the mathematical series function, without discontinuity at any point to an anterior lens surface, a posterior lens surface and an equatorial region of a crystalline lens described by crystalline lens profile data acquired by the input module.

2. The system of claim 1, wherein said data source is selected from the group consisting of: direct manual entry, electronic data entry, electronic data transfer and exchange from another device.

3. The system of claim 2, wherein the electronic data transfer or exchange is selected from the group consisting of: object linking and embedding (OLE), open database connectivity (ODBC), and a device for direct measurement of crystalline lens shape.

4. The system of claim 1, wherein the device for direct measurement of lens shape is selected from the group consisting of: optical coherence tomography (OCT), ultrasonography, profilometry, and combinations thereof.

5. The system of claim 1, wherein said receptacle is selected from the group consisting of: direct manual data output, electronic data output, electronic data transfer or exchange to another device.

6. The system of claim 5, wherein said electronic data transfer or exchange to another device is selected from the group consisting of: object linking and embedding (OLE), open database connectivity (ODBC).

7. The system of claim 1, wherein said lens shape is selected from the group consisting of: a crystalline lens shape and a prosthetic lens shape.

8. The system of claim 1, wherein the device for direct output of lens shape is selected from the group consisting of: CAD devices, CAM devices, and combinations thereof.

9. The system of claim 8, wherein the output device for direct output of lens shape is selected from the group consisting of: lathes, mills, cameras, plotters, and combinations thereof.

10. The system of claim 1, wherein the lens is a crystalline lens.

11. The system of claim 1, wherein the lens design is a crystalline lens prosthetic design.

12. The system of claim 1 wherein the lens profile data indicates that the lens is laterally asymmetric, and the lens profile description includes rotational asymmetry.

13. The system of claim 12 wherein said lateral asymmetry is described using an offset parameter that varies according to an order of the base function.

* * * * *